United States Patent
Nagamoto

[11] Patent Number: 6,063,118
[45] Date of Patent: May 16, 2000

[54] CAPSULAR ADHESION PREVENTING RING

[76] Inventor: Toshiyuki Nagamoto, 2-29-23 Nozawa Setagaya, Tokyo 154, Japan

[21] Appl. No.: 09/057,440

[22] Filed: Apr. 9, 1998

[30] Foreign Application Priority Data

Jul. 19, 1997 [JP] Japan ................................. 9-209880
Dec. 29, 1997 [JP] Japan ................................. 9-369267

[51] Int. Cl.⁷ .............................. A61F 2/14; A61B 19/00
[52] U.S. Cl. ................ 623/4; 623/5; 623/6; 128/898
[58] Field of Search ........................ 623/6, 5, 4

[56] References Cited

U.S. PATENT DOCUMENTS

| | | |
|---|---|---|
| Re. 31,626 | 7/1984 | Hoffer . |
| Re. 31,998 | 10/1985 | Myers . |
| 4,316,291 | 2/1982 | Severin . |
| 4,562,600 | 1/1986 | Ginsberg et al. . |
| 4,725,276 | 2/1988 | Bissonette et al. . |
| 4,880,427 | 11/1989 | Anis . |
| 5,275,624 | 1/1994 | Hara et al. ................... 623/6 |
| 5,326,347 | 7/1994 | Cumming . |
| 5,366,501 | 11/1994 | Langerman . |
| 5,465,737 | 11/1995 | Schachar ................... 128/898 |
| 5,549,670 | 8/1996 | Young et al. . |
| 5,562,731 | 10/1996 | Cumming . |
| 5,593,436 | 1/1997 | Langerman . |
| 5,693,094 | 12/1997 | Young et al. ................ 623/6 |

FOREIGN PATENT DOCUMENTS

| | | |
|---|---|---|
| 3-504444 | 10/1991 | Japan . |
| 4-36484 | 12/1992 | Japan . |
| 5-58118 | 8/1993 | Japan . |
| 6-9582B2 | 2/1994 | Japan . |
| 8-508913 | 9/1996 | Japan . |
| 10-211 | 1/1998 | Japan . |

*Primary Examiner*—Mickey Yu
*Assistant Examiner*—Hieu Phan

[57] ABSTRACT

The capsular adhesion preventing ring includes a wristband-like member having a diameter larger than that of an anterior capsular opening. The ring has multiple engaging holes and multiple guide slots formed through the circumferential wall of the ring, and each guide slot extends from the lower or upper rims of the ring to a corresponding engaging hole. In this ring, each guide slot may have a slant angle to the rim of the ring, be opened to a corresponding engaging hole along a cutting line of the hole, and an engaging protrusion may be formed between the guide slot and engaging hole. The direction of the engaging holes and guide slots from inside to outside of the wall may be almost parallel to the direction of a corresponding part of the loops of the intraocular lens that is inserted into the capsular bag before the insertion of the ring. This ring prevents adhesion of the capsular bag, which is adopted to prevent adhesion of the anterior and posterior lens capsules at the incised edge of the anterior capsule after cataract surgery, and also prevents lens regeneration, so as to prevent secondary cataracts.

10 Claims, 4 Drawing Sheets

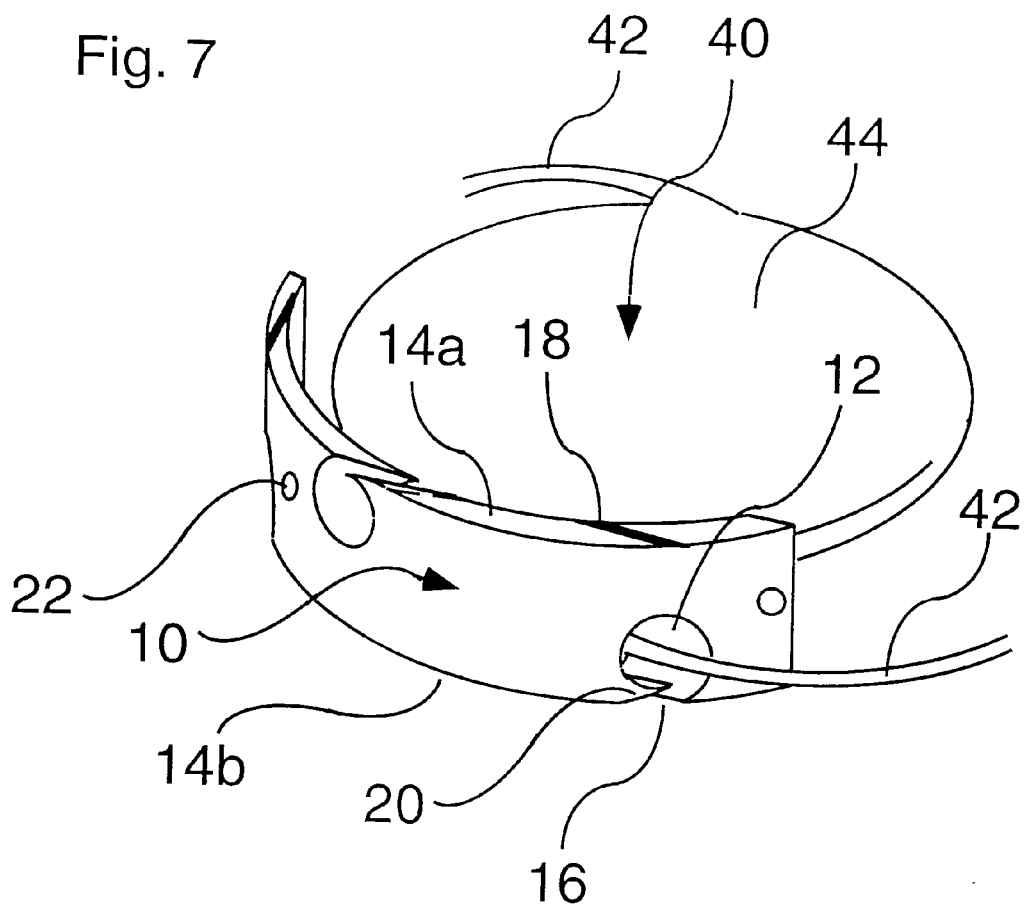

CAPSULAR ADHESION PREVENTING RING

TECHNICAL FIELD

The present invention relates to a ring for preventing adhesion of the capsular bag of the crystalline lens, which contributes to prevent secondary cataracts that is a postoperative complication after cataract surgery.

BACKGROUND OF THE INVENTION

When visual function or acuity is declined because of cataract, a general method to improve the impaired vision is a surgery. In the current cataract surgeries, an intraocular lens is inserted into the capsular bag after removal of the central anterior lens capsule, lens nucleus and cortex, so as to substitute for the refractive function of the crystalline lens.

As one of the postoperative problems, opacification frequently occurs along the capsular bag, and visual function or acuity is impaired if the opacity reaches the pupillary area. This is called secondary cataracts or after-cataracts. The reduction of visual function due to the secondary cataracts has been a serious problem in the medical field though there have been no effective preventions for surely avoiding occurrence of the secondary cataract.

Clinically significant secondary cataracts are classified into two types, namely, capsular fibrosis and Elschnig's pearls. The capsular fibrosis is white-color fibrous opacity composed of extracellular matrices such as collagens. Some lens epithelial cells transdifferentiate into myofibroblast-like cells after cataract surgery, and they produce a large quantity of extracellular matrices including collagens, which cause fibrous opacity to appear inside and outside of the capsular bag.

The lens epithelial cells exist only under the anterior lens capsule in normal conditions. During cataract surgery, a circular opening is made at the center of the anterior lens capsule. This is called an anterior capsulotomy. The transdifferentiation of lens epithelial cells into myofibroblast-like cells mainly occurs around the incised edge of the anterior capsule. The anterior capsulotomy margin adheres to the posterior lens capsule through the extracellular matrices secreted by the transdifferentiated cells. When a large number of cells transdifferentiate around the anterior capsulotomy margin, the fibrous opacity composed of extracellular matrices can reach the pupillary area and impair the visual function.

Since the entire anterior capsulotomy margin adheres to the posterior capsule, a closed space surrounded by the anterior and posterior lens capsules is formed outside the adhered region. In this closed space, the lens epithelial cells can proliferate, differentiate into lens fiber cells, and a crystalline lens gradually regenerates. The bulk of regenerated lens is composed of newly formed lens fiber cells. If the closed space is filled with the regenerated lens fiber cells, these cells are extruded from the closed space to the open space on the posterior capsule (the posterior chamber) through the holes in the fibrous net of extracellular matrices at the adhesive region around the capsulotomy margin. They expand on the posterior lens capsule, where they are exposed to the aqueous humor. Due to the influence of the aqueous humor, the extruded lens fiber cells swell and induce fusion of plasma membrane, and form so-called Elschnig's pearls, which undesirably scatter the light passed through the cornea and disturb visual function.

SUMMARY OF THE INVENTION

It is therefore an object of the present invention to provide a ring for preventing adhesion of the capsular bag of a crystalline lens, which is adopted to prevent adhesion of the anterior and posterior lens capsules at the incised edge of the anterior lens capsule after cataract surgery, and also prevent regeneration of crystalline lens, so as to prevent secondary cataracts.

A capsular adhesion preventing ring according to the present invention comprises a wristband-like member having an inner diameter that is larger than that of an anterior capsular opening. The ring has multiple engaging holes and multiple guide slots formed through the circumferential wall of the wristband-like member, and each guide slot extends from a corresponding engaging hole to the lower or upper rim of the wristbandlike member.

The wristband-like member should be located outside of an intraocular lens optic which is inserted into the capsular bag before insertion of the ring. The ring is designed for supporting the anterior capsule from an inside of the capsular bag to keep the anterior capsulotomy edge away from the posterior lens capsule. Accordingly, the inner diameter of the ring is slightly larger than that of the intraocular lens optic and that of the anterior capsular opening.

The diameter of the engaging holes in the ring is preferably larger than a thickness of a corresponding part of a loop of the intraocular lens that is inserted into the capsular bag before the insertion of the ring. The engaging holes are preferably located at equal intervals. Too many engaging holes induce decrease in rigidity of the wristband-like member, and too few engaging holes lead to longer time to engage a loop of the intraocular lens inserted before the insertion of the ring with the engaging hole and decrease the effect inducing aqueous humor circulation within the capsular bag. Because of these points, it is preferable that the number of the engaging holes is between 4 and 12.

The width of the guide slot opening at the rim is larger than a thickness of a corresponding part of a loop of the intraocular lens that is inserted into the capsular bag before the insertion of the ring. Each of the guide slots in the ring has a slant angle to the rim of the ring. Each of the guide slots is opened to a corresponding engaging hole along a cutting line of the hole. An engaging protrusion is preferably formed between each of the guide slots and the corresponding engaging hole to hold loops of the inserted intraocular lens inside the engaging hole.

The guide slots could be located at one side of the rim, or alternately at both upper and lower rims. When the engaging holes and guide slots are alternately located in the upper and lower portions of the circumferential wall of the ring, the ring is preferably designed to be the same configuration if the ring is turned upside down.

The direction of the engaging holes and guide slots from inside to outside of the wall of the ring is preferably almost parallel to the direction of a corresponding part of the loops of the intraocular lens that is inserted into the capsular bag before the insertion of the ring.

The ring preferably has marks on the rim of the ring, and each of the marks indicate each position of a corresponding guide slot opening in the opposite rim of the ring. The ring preferably has insertion holes or grooves in or on the wall of the ring to engage with an instrument for insertion of the ring into the capsular bag.

The ring is preferably made of an elastic or flexible material such as poly (2hydroxyethylmethacrylate), copolymer of phenylethylacrylate and phenylmethylacrylate or silicone, which has little or no toxicity to the ocular tissues surrounding the lens when the ring is inserted inside the capsular bag.

The ring preferably has insertion holes or grooves in or on the wall of the ring to engage with an instrument for insertion of the ring into the anterior chamber and/or capsular bag.

BRIEF DESCRIPTION OF THE DRAWINGS

FIG. 7 is a perspective view showing the capsular adhesion preventive ring of FIG. 2 and a loop of an intraocular lens which engages with the ring.

DETAILED DESCRIPTION OF THE PREFERRED EMBODIMENT

Figure 1:
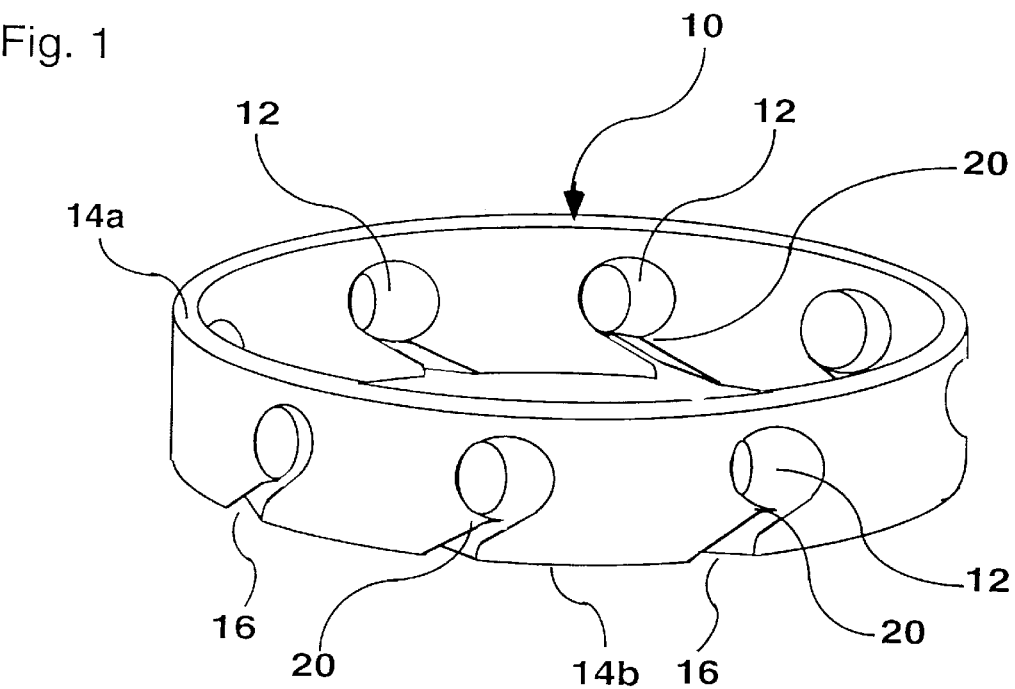
FIG. 1 is a perspective view of the capsular adhesion preventive ring according to one embodiment of the present invention.
Figure 2:
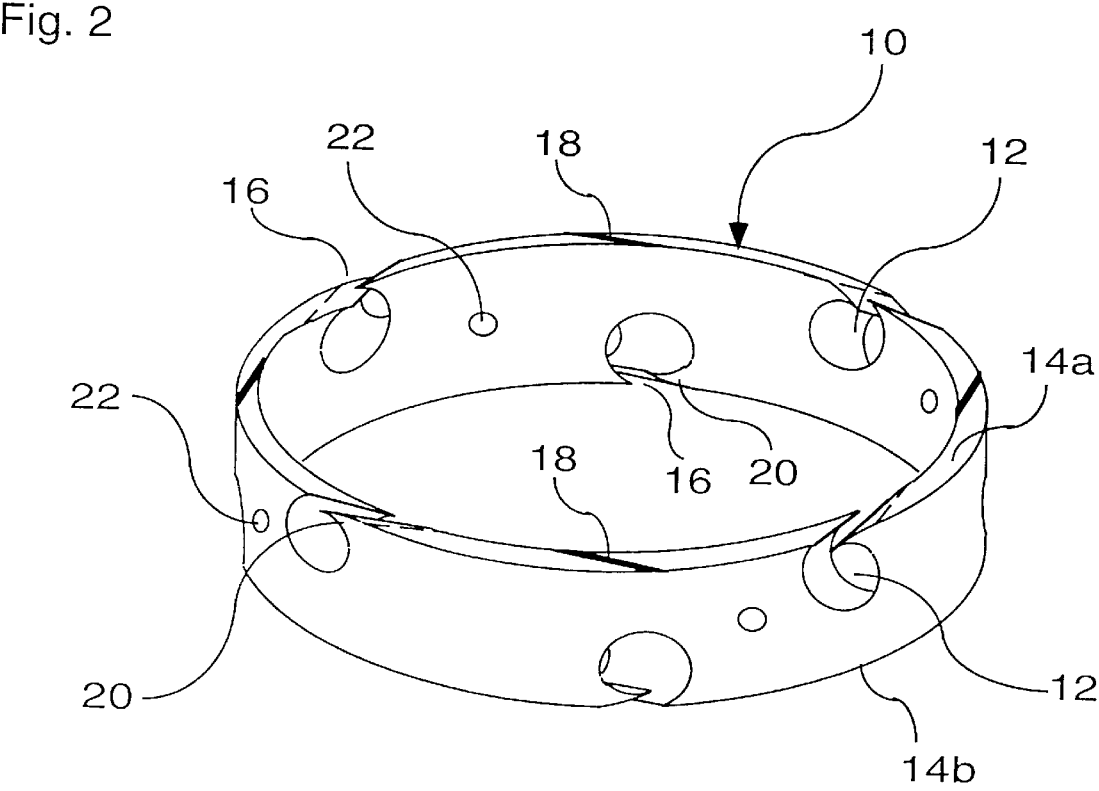
FIG. 2 is a perspective view of the capsular adhesion preventive ring according to another embodiment of the present invention.

FIG. 1 is a perspective view of the ring for preventing adhesion of the capsular bag of the crystalline lens according to one preferred embodiment of the present invention. FIG. 2 is a perspective view of the ring for preventing adhesion of the capsular bag of the crystalline lens according to another preferred embodiment of the present invention. As shown in FIGS. 1 and 2, this ring 10 consists of a wristband-like member having eight engaging holes 12 and eight guide slots 16 formed through its circumferential wall. The guide slots 16 are formed obliquely to extend from the respective holes 12 toward the lower rim 14b of the ring 10. The engaging holes 12 and eight guide slots 16 are located at equal intervals. Although both numbers of engaging holes 12 and guide slots 16 are eight in FIG. 1, the numbers are not restricted thereto, and are preferably selected from 4 to 12. Whereas the guide slots 16 are located at only one side of the rims 14b of the ring in FIG. 1, these guide slots 16 could also be alternately positioned at both sides of the rims 14a and 14b as shown in FIG. 2. When the ring 10 is made as shown in FIG. 2, the ring 10 has the same configuration if the ring 10 is turned upside down, and is able to be inserted inside the capsular bag 30 without paying attention to whether the ring 10 is upside or downside. The ring 10 preferably has insertion holes 22 or grooves in or on the wall of the ring 10 to engage with an instrument for insertion of the ring 10 into the capsular bag 30.

Figure 3:
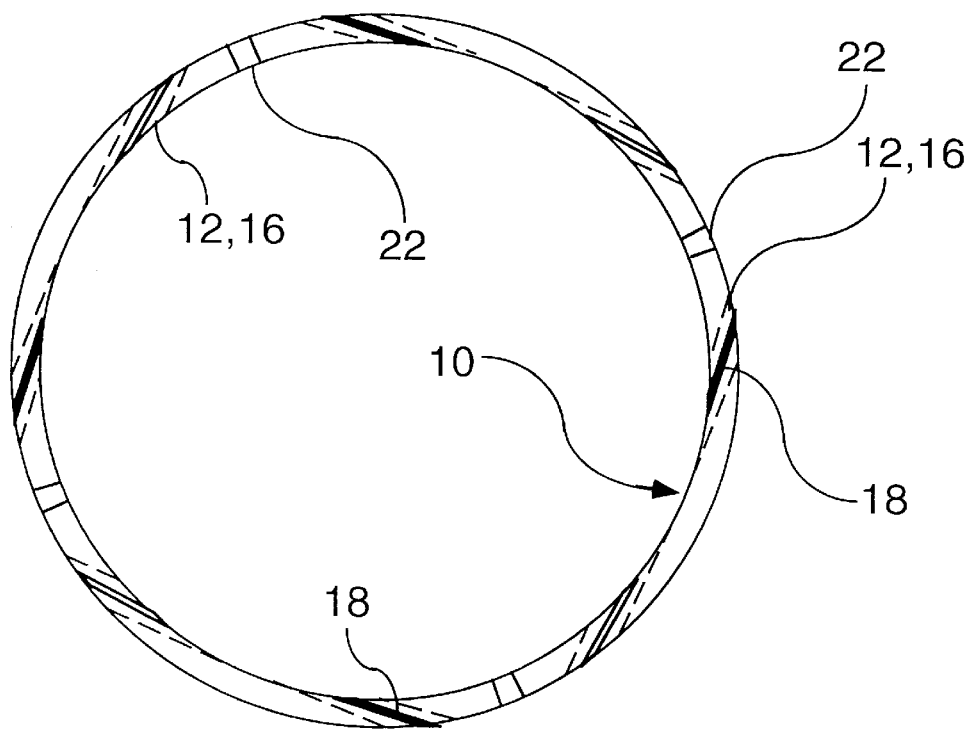
FIG. 3 is a plan view of the capsular adhesion preventive ring of FIG. 2.

FIG. 3 is a plan view of the capsular adhesion preventive ring of FIG. 2. As shown in FIGS. 2 and 3, marks 18 indicating the position of the guide slots opening 16 in the opposite rim of the ring are preferably made on both sides of the rims 14a and 14b. The marks 18 enable the surgeon to easily insert the loop of an intraocular lens into the guide slot 16 and engage the lens with the engaging hole 12.

Figure 4:
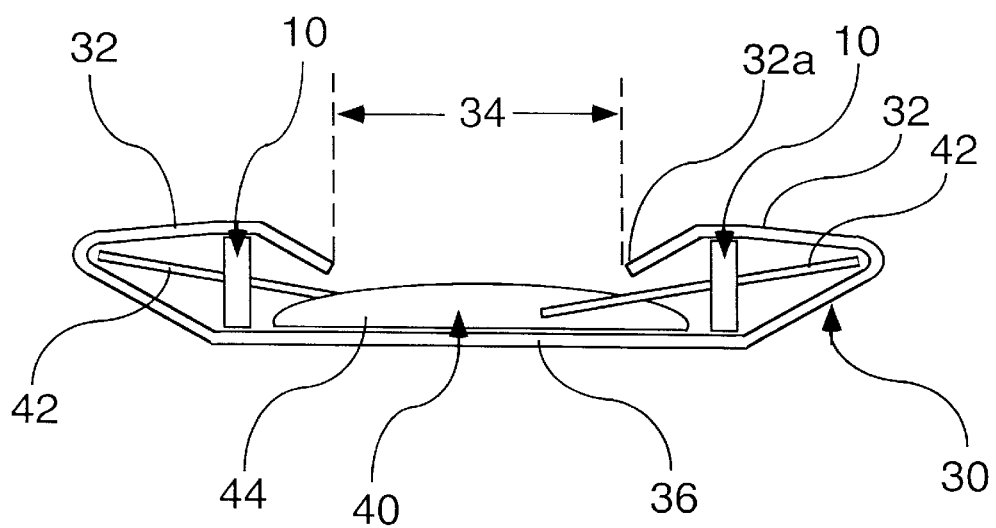
FIG. 4 is a side view showing the capsular adhesion preventive ring of FIG. 2 when it is inserted into the capsular bag along with an intraocular lens optic.
Figure 5:
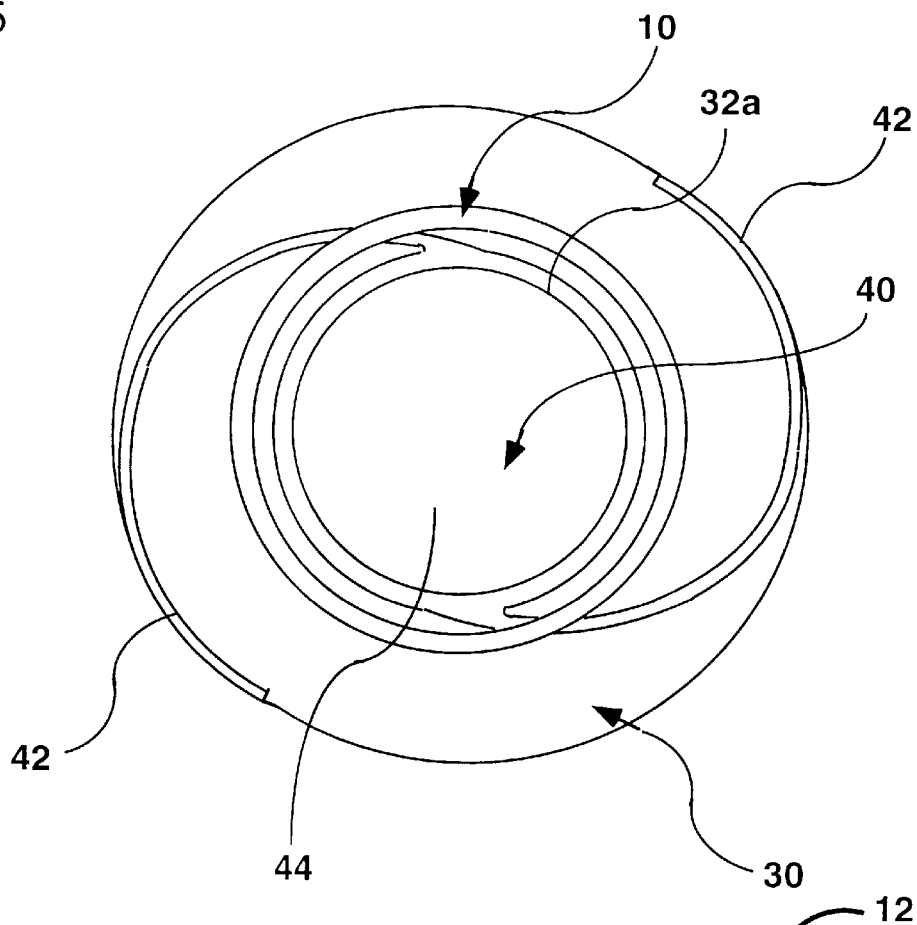
FIG. 5 is a plan view showing the capsular adhesion preventive ring of FIG. 2 when it is inserted into the capsular bag along with an intraocular lens optic.

FIGS. 4 and 5 are side and plan views, respectively, showing the capsular adhesion preventive ring of FIG. 2, when it is inserted into the capsular bag along with an intraocular lens optic. In FIGS. 4 and 5, an intraocular lens 40 is already inserted inside the capsular bag 30 through the anterior capsular opening 34 made at the center of the anterior capsule 32 of the lens capsule 30. As shown in FIGS. 4 and 5, the ring 10 has a diameter that is larger than the diameter of a optic 44 of the intraocular lens 40 that is inserted into the capsular bag 30 before the insertion of the ring 10, and also larger than the diameter of an anterior capsular opening 34.

Figure 6:
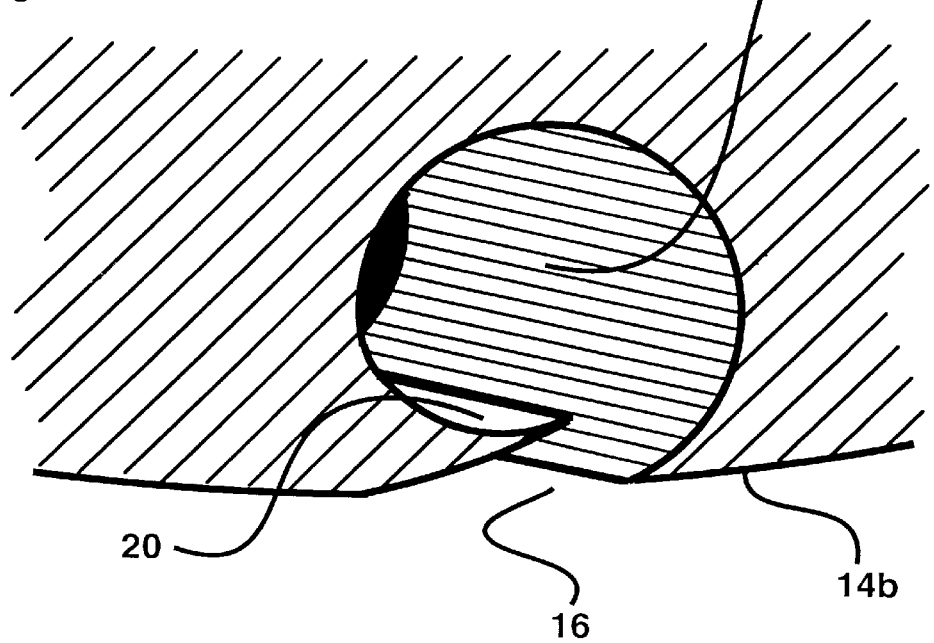
FIG. 6 is a magnified view of the engaging hole, guide slot and engaging protrusion of the capsular adhesion preventive ring of FIG. 2.

FIG. 6 is a magnified view of the engaging hole, guide slot, and engaging protrusion of this ring 10. As shown in FIG. 6, the engaging hole 12 and guide slot 16 are formed through the entire thickness of the circumferential wall of the ring 10. The guide slot 16 has a slant angle to the rim 14a or 14b of the ring 10, and is opened to a corresponding engaging hole 12 along a cutting line of the engaging hole 12. An engaging protrusion 20 is formed between the guide slot 16 and the corresponding engaging hole 12.

FIG. 7 is a perspective view showing a part of the capsular adhesion preventive ring of FIG. 2 and a loop of an intraocular lens which engages with the ring. As shown in FIG. 7, the direction of the engaging hole 12 and guide slot 16 from inside to outside of the wall of the ring 10 is preferably almost parallel to the direction of a corresponding part of loops 42 of the intraocular lens 40 that is inserted into the capsular bag 30 before the insertion of the ring 10. As a result, the engaging hole 12 and guide slot 16 are formed with a slant angle to the wall of the ring 10.

In order to smoothly engage the loop 42 of an intraocular lens 40 with the engaging hole 12 through the guide slot 16, the width of the guide slot 16 at the rim 14a or 14b and the diameter of the engaging holes 12 are larger than the thickness of a corresponding part of a loop 42 of an intraocular lens 40 that is inserted into the capsular bag 30 before the insertion of the ring 10.

The ring 10 is preferably made of an elastic or flexible material which has little or no toxicity to the ocular tissues surrounding the lens when the ring 10 is inserted inside the capsular bag 30, for example poly (2-hydroxyethylmethacrylate).

A method for inserting the capsular adhesion preventive ring 10 into the capsular bag 30 will be now described.

Initially, the intraocular lens 40 is inserted into the capsular bag 30 according to a known method, and then the capsular adhesion preventing ring 10 is inserted using an insertion instrument. As one possible inserting method, the ring 10 is inserted into the anterior chamber through the corneoscleral or corneal incision then inside the capsular bag 30 as engaging (a part of) the tip(s) of an insertion instrument with insertion hole(s) 22 or groove(s) in or on the wall of the ring 10. As shown in FIGS. 4 and 5, the ring 10 is positioned outside of the intraocular lens optic 28, and should be located as coaxial as possible with the optic 28. After the ring 10 is inserted inside the capsular bag, the loops 26 of the intraocular lens 24 are guided into the engaging holes 12 through the guide slots 14. When the marks of guide slot 18 are made at the rim 14a or 14b opposite to the corresponding guide slot 16, the marks 18 could be utilized as indicators for insertion of the loop 42 of an intraocular lens 40. The loops 42 guided into the guide slots 16 pass over the engaging protrusions 20 before entering the engaging holes 12.

The loop 42 is elastic and has rigidity enough to support an intraocular lens 40 inside the capsular bag 30. After the loops 26 are received in the engaging holes 12, the loops 26 are locked or retained in the corresponding engaging holes 12 due to the corresponding engaging protrusions 16. As a result, the ring 10 is located outside of the optic 28, supported by the loops 26, and supports the anterior capsulotomy margin 32a away from the posterior capsule 36.

When the ring 10 is inserted inside the capsular bag 30, the aqueous humor can go inside and outside of the ring 10, namely circulate inside of the entire capsular bag 30, through the engaging holes 12 and guide slots 16. Circulation of aqueous humor and no closed space inside the capsular bag inhibit regeneration of lens fiber cells.

According to the present invention, the adhesion of the anterior and posterior lens capsules at the incised edge of the anterior capsule after cataract surgery can be avoided, and the progression of fibrous opacity from the incised edge of the anterior lens capsule to the center of the posterior capsule can be avoided. It is thus possible to prevent impairment of visual function due to the fibrous opacity on the posterior lens capsule.

Further, according to the present invention, the adhesion of the anterior and posterior lens capsules at the incised edge of the anterior lens capsule after cataract surgery can be avoided, and no closed space is formed in the capsular bag. In this condition, since the aqueous humor circulates inside of the entire capsular bag through the engaging holes and guide slots of the ring, regeneration of lens fiber cells does not occur, and visual impairment due to Elschnig's pearls can be advantageously prevented.

Furthermore, according to the present invention, when the guide slots are alternately made at the rim of the ring, the ring can be inserted inside the capsular bag without paying attention to the up- or downside of the ring, because the configuration of the ring is the same if the ring is turned upside down.

Furthermore, according to the present invention, when the marks of the guide slots are made at the rim opposite to the corresponding guide slot, the loops of an intraocular lens can be easily guided into the guide slots, and easily engaged with the engaging holes.

Although only two embodiments of the invention have been illustrated and described, it will be apparent to those skilled in the art that various changes and modifications may be made to the embodiment without departing from the spirit and scope of the invention as defined in the appended claims.

I claim:

1. A capsular adhesion preventing ring, comprising:
    a wristband-like member having a diameter larger than that of an anterior capsular opening, said wristband-like member having multiple engaging holes and multiple guide slots formed through the circumferential wall of the ring, each of said guide slots extending from a corresponding one of said engaging hole to lower or upper rim of said wristband-like member and forming an opening in said lower or upper rims.

2. The capsular adhesion preventing ring as defined in claim 1, wherein said guide slots are alternately opened at both sides of the rims.

3. The capsular adhesion preventing ring as defined in claim 1, wherein said upper or lower rim has marks of guide slot, and each of the marks indicates each position of a corresponding guide slot opening in the opposite rim of the ring.

4. The capsular adhesion preventing ring as defined in claim 1, wherein the direction of said engaging holes and said guide slots from inside to outside of the circumferential wall of the ring is adapted to be almost parallel to the direction of a corresponding part of the loops of the intraocular lens when it is inserted into the capsular bag, and each of said guide slots is opened to a corresponding one of said engaging holes along a mark of said engaging holes, and an engaging protrusion is formed between each of said guide slots and a corresponding one of said engaging holes.

5. The capsular adhesion preventing ring as defined in claim 1, wherein the diameter of said wristband-like member is controlled such that the member can support the anterior lens capsule from inside of the capsular bag.

6. The capsular adhesion preventing ring as defined in claim 1, wherein the diameter of said wristband-like member is larger than a diameter of an optic of an intraocular lens that is inserted into the capsular bag.

7. The capsular adhesion preventing ring as defined in claim 1, wherein said engaging holes have a diameter larger than a thickness of a corresponding part of a loop of the intraocular lens when it is inserted into the capsular bag.

8. The capsular adhesion preventing ring as defined in claim 1, wherein each of said guide slots has a slant angle to the rim of said wristband-like member.

9. The capsular adhesion preventing ring as defined in claim 1, wherein a width of an opening of said guide slots at the rim of said wristband-like member is larger than a thickness of a corresponding part of a loop of the intraocular lens that is inserted into the capsular bag.

10. The capsular adhesion preventing ring as defined in claim 1, wherein insertion holes or grooves are made in or on the circumferential wall of said wristband-like member to engage with an instrument when inserting the ring into the capsular bag.

* * * * *